(12) United States Patent
Shoemaker, Jr.

(10) Patent No.: US 11,478,377 B1
(45) Date of Patent: Oct. 25, 2022

(54) NO SLIP CONDOM CATHETER

(71) Applicant: Stephen P. Shoemaker Trust, Manhattan Beach, CA (US)

(72) Inventor: Stephen P Shoemaker, Jr., Redondo Beach, CA (US)

(73) Assignee: Stephen P. Shoemaker Trust, Manhattan Beach, CA (US)

( * ) Notice: Subject to any disclaimer, the term of this patent is extended or adjusted under 35 U.S.C. 154(b) by 0 days.

(21) Appl. No.: 17/689,716

(22) Filed: Mar. 8, 2022

(51) Int. Cl.
*A61F 5/453* (2006.01)
*A61F 5/44* (2006.01)

(52) U.S. Cl.
CPC ............ *A61F 5/453* (2013.01); *A61F 5/4408* (2013.01)

(58) Field of Classification Search
CPC ................................ A61F 5/453; A61F 5/4408
See application file for complete search history.

(56) References Cited

U.S. PATENT DOCUMENTS

| | | | | |
|---|---|---|---|---|
| 2,358,440 A | * | 9/1944 | Bowman | A61B 42/00 128/880 |
| 3,421,507 A | * | 1/1969 | Gresham | A61F 5/453 604/349 |
| 3,835,857 A | * | 9/1974 | Rogers, III | A61F 5/453 604/349 |
| 4,484,918 A | * | 11/1984 | Omley | A61F 5/453 604/349 |
| 4,540,409 A | * | 9/1985 | Nystrom | A61F 5/453 206/229 |
| 4,581,026 A | * | 4/1986 | Schneider | A61L 24/043 604/352 |
| 4,626,250 A | * | 12/1986 | Schneider | A61F 5/453 604/350 |
| 4,685,913 A | * | 8/1987 | Austin | A61F 5/453 604/353 |
| 4,769,020 A | * | 9/1988 | Eaton | A61F 5/453 604/352 |
| 4,790,834 A | * | 12/1988 | Austin | A61F 5/453 600/580 |
| 4,846,816 A | * | 7/1989 | Manfredi | A61F 5/4405 604/323 |
| 5,318,550 A | * | 6/1994 | Cermak | A61F 5/453 604/350 |
| 5,423,784 A | * | 6/1995 | Metz | A61F 5/453 604/351 |
| 5,520,671 A | * | 5/1996 | Bouser | A61F 5/453 604/351 |
| 5,618,277 A | * | 4/1997 | Goulter | A61F 5/453 604/350 |
| 5,645,541 A | * | 7/1997 | Bouser | A61F 5/453 604/351 |
| 5,662,631 A | * | 9/1997 | Marx | A61F 5/453 604/352 |

(Continued)

*Primary Examiner* — Guy K Townsend
(74) *Attorney, Agent, or Firm* — Fulwider Patton LLP

(57) ABSTRACT

A urinary catheter device is disclosed that uses a condom that is placed over the penis and connects to a tube that leads to a collection bag or container. To maintain the condom on the penis, the device includes a hinged sleeve that is placed over the condom on the shaft of the penis and prevents slipping. The sleeve is held in place by an elastic band, and the dry frictional contact between the condom, the sleeve, and the patient has been found to prevent the catheter device from slipping off the patient.

2 Claims, 4 Drawing Sheets

(56) References Cited

U.S. PATENT DOCUMENTS

| | | | | |
|---|---|---|---|---|
| 5,713,880 | A * | 2/1998 | Anderson | A61F 5/453 604/352 |
| 5,897,540 | A * | 4/1999 | Grundke | A61F 5/453 604/352 |
| 6,068,618 | A * | 5/2000 | Anderson | A61F 5/453 604/347 |
| 6,296,627 | B1 * | 10/2001 | Edwards | A61F 5/453 604/326 |
| 6,887,223 | B2 * | 5/2005 | Bisbee | A61F 5/453 224/148.2 |
| 7,014,635 | B2 * | 3/2006 | Goulter | A61F 6/00 604/346 |
| 7,077,833 | B2 * | 7/2006 | Bonham | A61F 5/44 604/323 |
| 7,087,043 | B2 * | 8/2006 | Dolan | A61F 5/453 604/351 |
| 7,160,276 | B2 * | 1/2007 | Bruns | A61F 5/451 604/339 |
| 7,186,245 | B1 * | 3/2007 | Cheng | A61F 5/44 604/350 |
| 10,016,299 | B2 * | 7/2018 | Pierson | A61F 5/4408 |
| 10,449,083 | B2 * | 10/2019 | Pierson | A61F 5/4404 |
| 10,675,175 | B2 * | 6/2020 | Holt | A61F 5/453 |
| 2006/0004332 | A1 * | 1/2006 | Marx | A61F 5/453 604/347 |

* cited by examiner

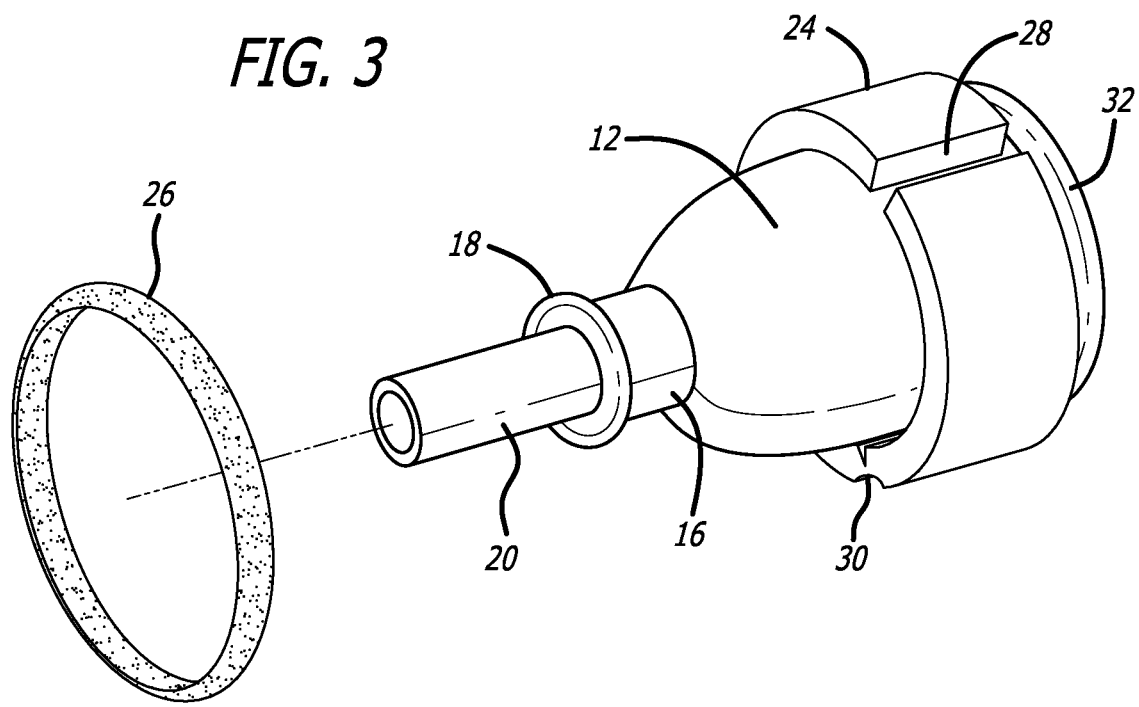
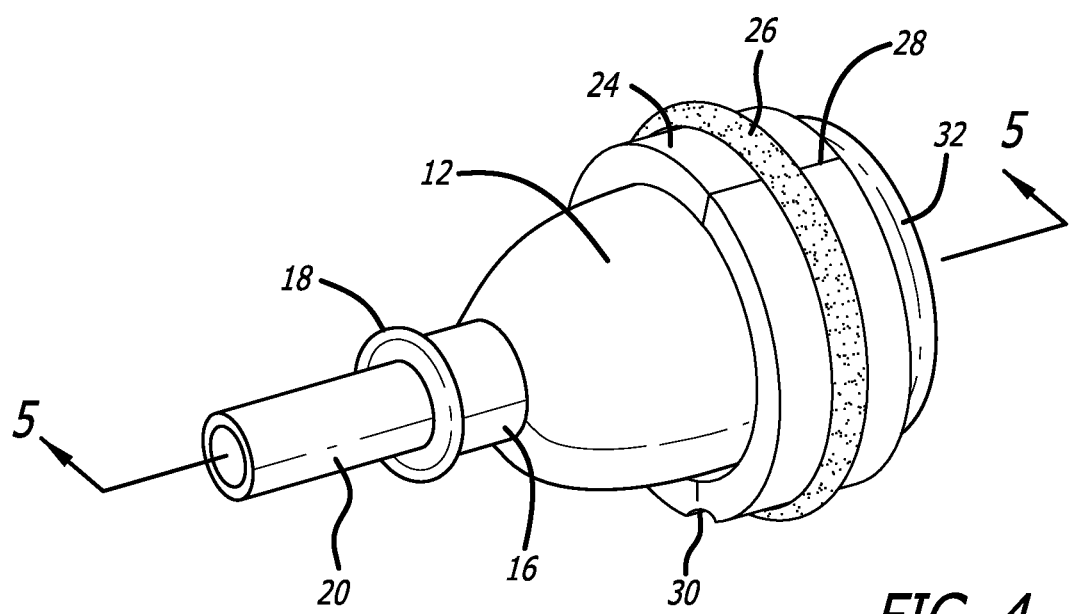

NO SLIP CONDOM CATHETER

BACKGROUND

The present invention relates generally to adult incontinence, and more particularly to a catheter that is designed to overlay the male penis and collect urine to prevent wetting clothing and bedding. To achieve this goal, the present invention combines a condom with a tube and a collection container. Condoms are commonly used to prevent pregnancy and disease during intercourse. The condom stays in place when the penis is engorged and erect. However, when a patient is asleep or in a weakened condition the penis is typically flaccid. This presents a problem as to how to keep the condom in place and prevent it from slipping off during urination and sleep. Applying too much pressure on the penis is dangerous as blood flow or other vital functions may be impaired.

Urinary incontinence (UI) is defined as the involuntary loss of urine. In men, age is a consistently reported risk factor for UI; however, it is not considered a normal consequence of aging. Overall, UI affects up to 30% of community dwelling older adults and more than 50% of nursing home residents. Despite its high prevalence, up to one-half of cases may not be reported because individuals with UI may not seek medical intervention. Embarrassment and the perception that UI is an expected consequence of aging are common factors in the failure to seek a solution or treatment. That reluctance is particularly strong in men, who often deem the problem to be associated with a loss of masculinity.

Urinary incontinence is categorized according to pathophysiology and clinical presentation. The four main categories are (1) stress urinary incontinence (SUI), (2) urge urinary incontinence (UUI), (3) overflow incontinence, and (4) functional incontinence. Mixed types of incontinence are common and may complicate diagnosis and treatment because of overlapping symptoms. Studies have found that UI significantly affects psychological well-being and health care-related quality of life. Urinary incontinence may impair sexual function, restrict activities, interfere with interpersonal relationships, decrease self-esteem, increase caregiver burden, increase financial burden, and cause anxiety or depression. It is a common precipitant of institutionalization in older adults.

Because of current demographic trends, UI is an increasingly common medical and socioeconomic problem. One place where the issue arises with great propensity is senior housing, where older patients often suffer moderate to severe UI due to a variety of physiological conditions. In men, incontinence is often related to prostate problems or treatments that become exacerbated in the elderly. Certain medical conditions, particularly those affecting the brain or nervous system, such as Alzheimer's, Parkinson's, Dementia, Multiple Sclerosis, brain damage, and spinal problems can also lead to incontinence. This is due to the nerve passageways to or from the brain becoming damaged. The result can be either an overactive bladder (the need to go often and frequently) or an under-active bladder (ineffective emptying leading to leakage). Diabetes and or a stroke can also bring on incontinence.

With aging, bladder capacity decreases, ability to control urination declines, involuntary bladder contractions (detrusor overactivity) occur more often, and bladder contractility is impaired. Thus, voiding becomes more difficult to postpone and tends to be incomplete. Post void residual volume increases in as much as ≤100 mL (normal <50 mL). A weakening of the endopelvic fascia often results as well. In men, the tendency for the prostate to enlarge with age causes the partial obstruction of the urethra, leading to incomplete bladder emptying and strain on the detrusor muscle. These changes occur in many normal, continent elderly males and may facilitate incontinence but do not cause it.

One challenge associated with male incontinence is the necessity for changing clothing, bedding, and other items that may become soiled due to uncontrollable urination. When a disabled patient has voided his urine, the caregiver must remove the patient's clothing and bedding while the patient is in a prone position. This can be challenging to the caregiver, who must lift the patient to remove the clothing and bedding while simultaneously trying to extract the soiled garments and sheets, blankets, etc. If the patient is large or overweight, the problem becomes magnified.

The U.S. Census Bureau estimates there are 76.4 million baby boomers, and the oldest of this generation, which includes those born between 1946 and 1964, are over 65 years old. For many of these people, adult diapers are a way to ameliorate the effects of moderate to severe incontinence. Adult diapers are a $7 billion global market, and sales have grown more than 8 percent over the past five years due to this increasing number of baby boomers entering their 70s and 80s. This trend appears to be rising as the stigma of wearing protective undergarments becomes less and the popularity of these products grow.

Diapers can be an unsatisfactory solution for several reasons. First, the previously raised issue that, once soiled, the patient must be changed like an infant by a caregiver who may not have the strength to move a full grown adult male. Changing a diaper can lead to the patient being moved in positions that may strain or injure the patient, particularly when moved by a caregiver with inadequate strength to properly maneuver a full grown adult male. Patients who go frequently can get ignored because of the challenges in changing the patient, leading to health issues as well.

What is needed is a simple, cost effective device that handles leakage and reduces the frequency in which this occurs resulting in the patient needing to be cleaned. The present invention is directed to preventing the condom from slipping off the penis.

SUMMARY OF THE INVENTION

The present invention is a condom catheter that uses a latex, silicone, or other material condom connected at its end to a tube. The condom is placed on the penis so that when the patient urinates the urine flows through the tube that leads to a collection bag or container. To keep the condom in place, the system includes a short sleeve that is open on one end and hinged at the other so that it can adjust to different inner diameters. Since the head of the penis is larger than the shaft, the hinged sleeve is placed on the condom between the head and the shaft of the penis. The sleeve is closed about the shaft and held closed with an elastic band so as not to apply much pressure, but instead relies on friction. Once secured between dry penis and the dry plastic tube, the condom is frictionally prevented from slipping. Very little, if any, pressure is used to create this the no-slip system.

BRIEF DESCRIPTION OF THE DRAWINGS

FIG. 3 is another exploded view of the embodiment of FIG. 1; and

FIG. 4 is an enlarged view of the embodiment; and

DETAILED DESCRIPTION OF THE PREFERRED EMBODIMENTS

Figure 1:
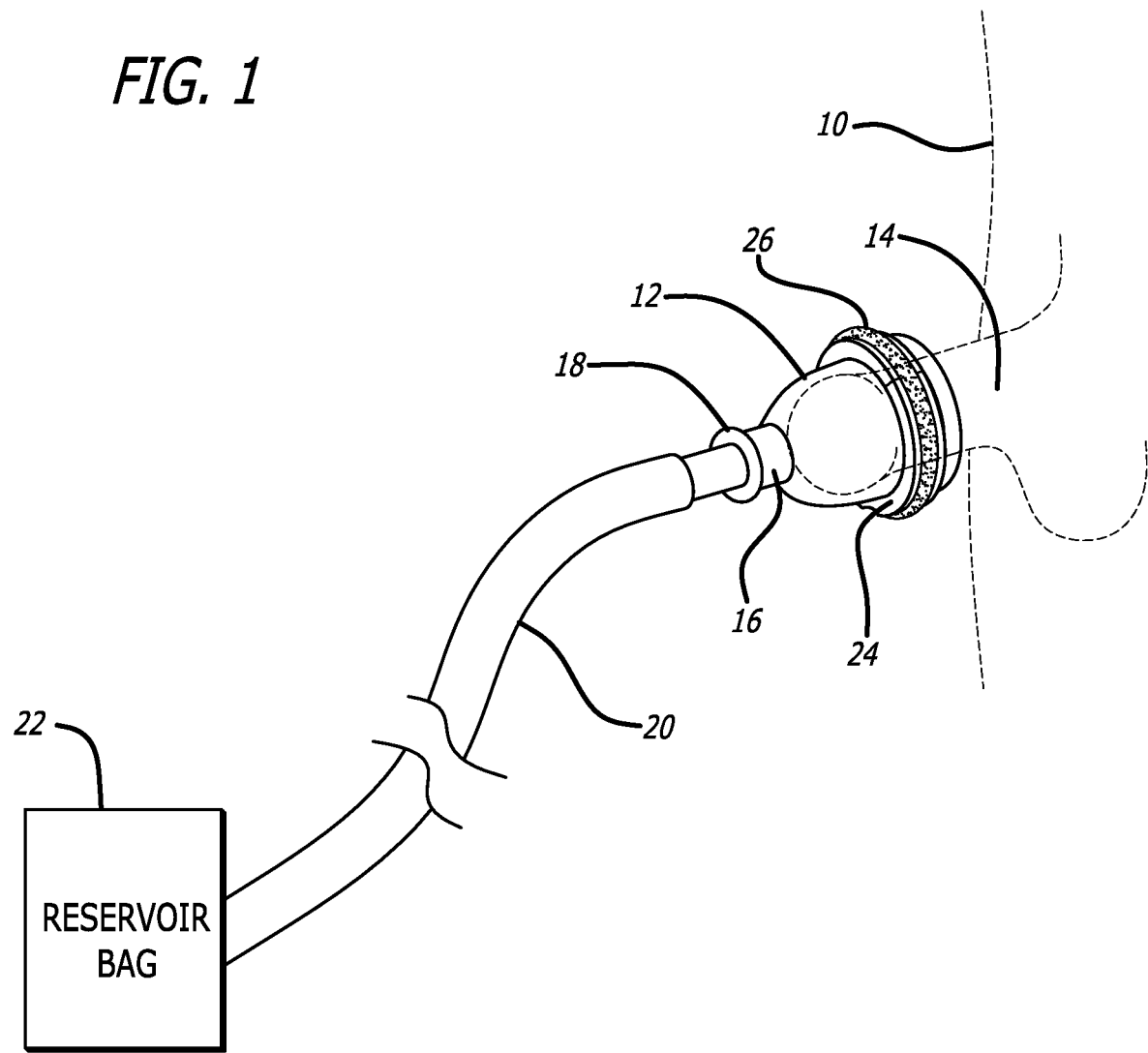
FIG. 1 is an elevated, perspective view of a first preferred embodiment of the present invention.

In a first preferred embodiment, the invention uses a latex or similar material condom to cover a male penis. Condoms are devices to protect the user from disease and to prevent procreation. The object is to protect the user from disease or stop the flow of ejaculation. Condoms are not designed to hold a tube or bag. The present invention solves this problem with a sleeve that creates a frictional stop by utilizing the dry skin, the dry condom, and the sleeve to frictionally hold the condom in place, but does not apply enough pressure to restrict blood flow or cause discomfort to the patient.

Urinary incontinence is embarrassing and unhealthy but can be prevented with the present invention which is reusable, easy, painless, and a reliable means of addressing this problem. The invention uses a condom with a tube attached to the end that connects to a container of some kind. The head of the penis being larger than the shaft causes a loose connection and the condom does not fit snuggly around the shaft of the penis. This loose fit causes slipping, leaking, and other problems. If the condom is small enough to fit the shaft snuggly it is difficult to get over the head. This could be addressed by using adhesives, tape, squeezing, pressure, etc. to prevent the condom catheter from leaking or slipping off the penis. However, adhesive and tapes are painful and squeezing or pressure are sometimes uncomfortable or dangerous.

FIGS. 1-5 depict a system for controlling incontinence that can be worn by a patient to prevent leakage of urine that might occur during sleep or during a period of incontinence. The patient 10 wears a secured urinary catheter that is formed using a common latex condom 12 that is worn on the patient's penis 14. Attached to the condom 12 at the reservoir tip is an annular coupling 16 including a collar 18 that is sized to receive a catheter tube 20 for conveying urine away from the sleeve or condom 12. The catheter tube 20 leads to a collection receptacle 22 such as a bag, jar, or bed pan.

Figure 2:
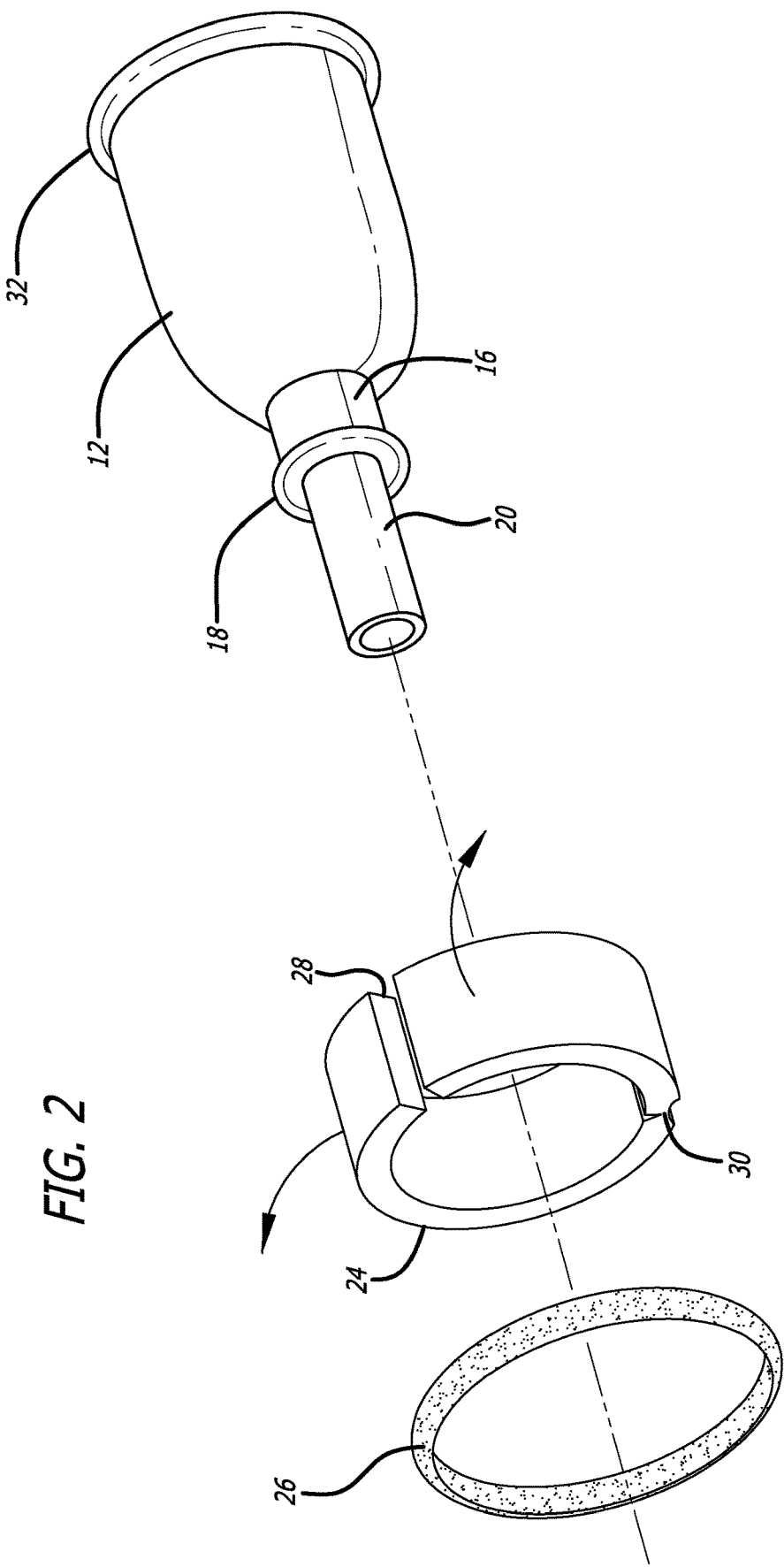
FIG. 2 is an enlarged, exploded view of the sleeve and sleeve of the embodiment of FIG. 1.
Figure 5:
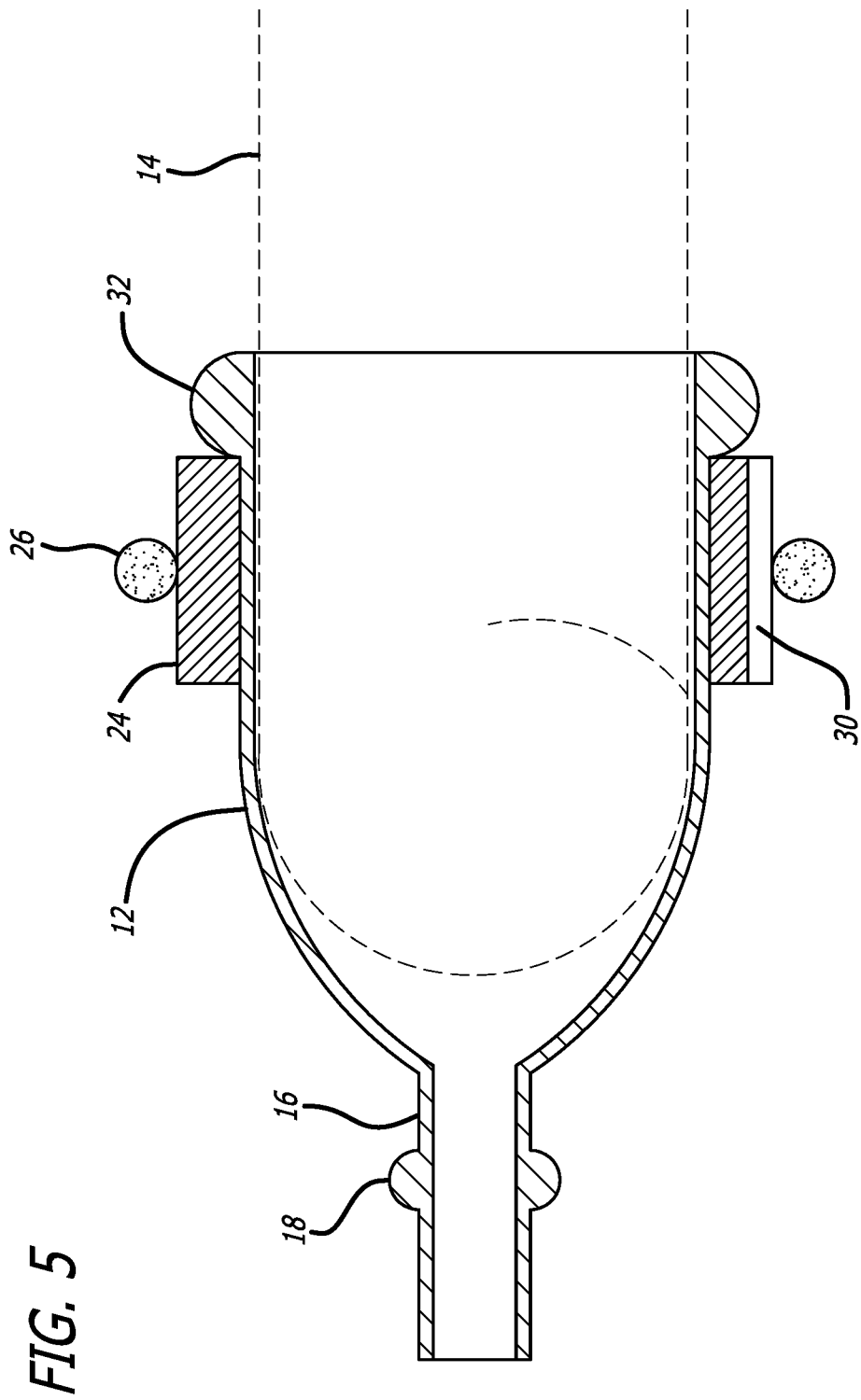
FIG. 5 is a cross sectional view taken along lines 5-5 of FIG. 4.

If the patient should release urine while asleep or otherwise unable to make it to a toilet, the urine transfers from the condom 12 through the annular coupling 16 and flows gravitationally through the catheter tube 20 into the container 22 such that the urine does not leak, soak the bedding, or soil the patient's other clothing. To keep the condom 12 on the penis 14, a hinged sleeve 24 is placed over the condom between the head and the base of the penis. As shown in FIG. 2, the sleeve 24 is cylindrical and plastic and pivots about a hinge portion 30, with a bias so that the respective free edges form a gap 28 and the hinge has a resiliency such that the sleeve flexes open and closed. With the condom on the patient, the sleeve 24 is opened and placed on the shaft of the penis, and then closed using an elastic band 26 or other closure mechanism. The combination of the condom and the hinged sleeve provides sufficient friction to prevent the condom from slipping off the user, and can easily be removed by taking off the elastic band and opening the sleeve 24. As shown in FIG. 3, the unused portion 32 of the condom helps to position the sleeve 24 on the penis. The invention greatly reduces trips to the bathroom, which occur often and are inconvenient, sometimes difficult, or even dangerous to the patient. The non-slip catheter provides the patient with an uninterrupted night's sleep.

While the inventor's preferred embodiments have been disclosed and described herein, the invention is not intended to be limited to the embodiments shown in the Figures or described herein. Rather, the spirit and scope of the invention is intended to include all such modifications and substitutions as would be readily apparent to a person of ordinary skill in the art at the time of this disclosure. Accordingly, unless expressly stated herein, nothing in this disclosure should be treated as limiting, and the scope of the invention is properly measured by the words of the appended claims using their customary and ordinary meanings.

I claim:

1. A urinary catheter, comprising:
    a condom configured to fit over a male penis, the condom including an annular coupling element;
    a conduit attached at a receiving end to the annular coupling element;
    a urine collection container attached at an exiting end of the conduit; and
    a hinged sleeve sized to fit over the condom, the hinged sleeve including a recess extending longitudinally along an entire length of an outer surface; and
    an elastic band to close the sleeve over the condom once the sleeve is in place.

2. The urinary catheter of claim 1, wherein the hinged sleeve bears against a rolled up portion at a base of the condom.

* * * * *